United States Patent [19]

Jelich et al.

[11] Patent Number: 5,091,068

[45] Date of Patent: Feb. 25, 1992

[54] PREPARATION OF 3-TRICHLOROMETHYL-PYRIDINE

[75] Inventors: Klaus Jelich, Wuppertal; Hans Lindel, Leverkusen, both of Fed. Rep. of Germany

[73] Assignee: Bayer Aktiengesellschaft, Leverkusen, Fed. Rep. of Germany

[21] Appl. No.: 590,387

[22] Filed: Sep. 28, 1990

[30] Foreign Application Priority Data

Oct. 20, 1989 [DE] Fed. Rep. of Germany ....... 3934957

[51] Int. Cl.⁵ .................. C07C 401/00; C07C 211/72
[52] U.S. Cl. ................. 204/157.64; 546/346
[58] Field of Search ............... 546/248, 346; 204/157.64

[56] References Cited

U.S. PATENT DOCUMENTS

| | | | |
|---|---|---|---|
| 3,412,095 | 11/1968 | Clark | 546/346 |
| 3,461,125 | 8/1969 | Kollonitsch | 546/346 |
| 4,288,599 | 9/1981 | Nishiyama et al. | 546/346 |
| 4,417,055 | 11/1983 | Nishiyama et al. | 546/346 |
| 4,420,434 | 12/1983 | Falk | 546/248 |

FOREIGN PATENT DOCUMENTS

| | | | |
|---|---|---|---|
| 0065358 | 11/1982 | European Pat. Off. | 546/346 |
| 1294362 | 3/1964 | France | 546/346 |

Primary Examiner—Mary C. Lee
Assistant Examiner—Robert C. Whittenbaugh
Attorney, Agent, or Firm—Sprung Horn Kramer & Woods

[57] ABSTRACT

A process for the preparation of 3-trichloromethylpyridine of the formula

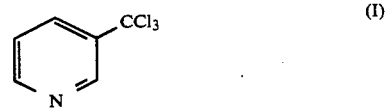

(I)

which comprises reacting 3-methyl-pyridine hydrogen sulphate of the formula

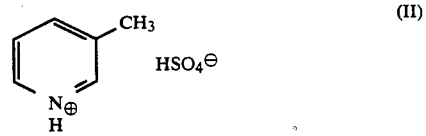

(II)

with elemental chlorine with exposure to at least one of visible and ultraviolet light at a temperature between about 70° C. and 150° C.

8 Claims, No Drawings

PREPARATION OF 3-TRICHLOROMETHYL-PYRIDINE

The invention relates to a new process for the preparation of 3-trichloromethyl-pyridine, which can be used as an intermediate for the preparation of known herbicides and insecticides.

It is known that 3-trichloromethyl-pyridine is obtained by heating nicotinic acid with phosphorus(V) chloride at 115° C. (cf. J. Chem. Soc. Perkin Trans I, 1989, 283–287) or by reacting phenyldichlorophosphane ($C_6H_5PCl_2$), phosphorus(III) chloride and chlorine at temperatures between 100° C. and 250° C. (cf. U.S. Pat. No. 4,634,771). However, the yields which can be achieved with these processes are not satisfactory; moreover, the use of phosphorus compounds presents problems since they cause pollution of the waste water.

Furthermore, it is known that 3-trichloromethyl-pyridine can also be obtained by reacting 3-methyl-pyridine with chlorine in the presence of a metal oxide catalyst or metal chloride catalyst at temperatures between 200° C. and 350° C. (cf. EP-A 65,358). However, the reaction does not proceed uniformly, and the product mixtures which are formed can only be separated with difficulty.

Furthermore, it is known that 3-methyl-pyridine can also be converted into 3-trichloromethyl-pyridine by chlorination in a mixture of sulphuric acid/oleum at 70° C. to 75° C., with exposure to light (cf. FR-A-1,394,362). However, it has been shown that in this process, too, mixtures of products which are difficult to separate are formed.

It has now been found that 3-trichloromethyl-pyridine, of the formula (I),

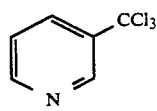

(I)

is obtained in a very good yield and in high purity when 3-methyl-pyridine hydrogen sulphate, of the formula (II),

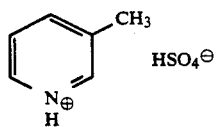

(II)

is reacted with elemental chlorine with exposure to visible and/or ultraviolet light, if appropriate in the presence of a catalyst, at temperatures between 70° C. and 150° C.

Surprisingly, 3-trichloromethyl-pyridine can be prepared in a relatively simple manner in a very good yield and in high purity by the process according to the invention, while, using the known processes, this product is obtained in moderate yields and in unsatisfactory quality.

The advantages of the processes according to the invention are, on the one hand, the use of 3-methyl-pyridine as a base compound, which is considerably more economical compared with nicotinic acid, and on the other hand, the low polution of waste water compared with the chlorination in sulphuric acid/oleum, combined with a high space-time yield.

The course of the process according to the invention can be outlined by the following equation:

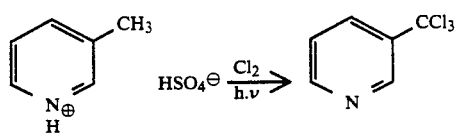

3-Methylpyridine hydrogen sulphate, of the formula (II), which is to be used as starting compound, has hitherto not been described in the literature as a defined chemical species, but can be obtained in a simple manner by combining (approximately) equimolar amounts of 3-methyl-pyridine and sulphuric acid, if appropriate with the use of a diluent, such as, for example, benzene, toluene, ethyl acetate and/or dioxane, at temperatures between 20° C. and 100° C.

3-Methyl-pyridine hydrogen sulphate, of the formula (II), can be prepared in a preceding reaction step and isolated as a pure product; however, it can also be reacted with chlorine in accordance with the process according to the invention without intermediate isolation.

If appropriate, the process according to the invention is carried out in the presence of a catalyst. Catalysts which can be used are virtually all catalysts which are suitable for reactions of this type. Catalysts which are preferably employed in the process according to the invention are carboxamides, in particular aromatic carboxamides, such as, for example, benzamide.

The process according to the invention is carried out with exposure to light. Suitable means for exposure are virtually all those customary in photochemical reactions. Light sources which are preferred in the process according to the invention are, in particular, those which emit light at the border between visible and ultraviolet light. This means that ordinary light bulbs are also suitable for exposure in the process according to the invention.

In general, the process according to the invention is carried out at temperatures between 70° C. and 150° C., preferably between 90° C. and 130° C. In general, the process according to the invention is carried out under atmospheric pressure. However, it is also possible to carry out the process under increased or reduced pressure, preferably between 0.1 and 10 bar.

To carry out the process according to the invention, 3 to 15 moles, preferably 3 to 10 moles, of chlorine are generally employed per mole of 3-methyl-pyridine hydrogen sulphate, of the formula (II).

In a preferred embodiment of the process according to the invention, the 3-methyl-pyridine hydrogen sulphate, of the formula (II), is initially prepared by introducing 3-methyl-pyridine into the reaction vessel and adding an approximately equimolar amount of sulphuric acid at temperatures between 20° C. and 100° C. The reaction temperature required is then established—if appropriate after a catalyst has been added—, and chlorine is then slowly passed in with exposure to light until the reaction is virtually complete.

After cooling, the mixture is diluted with water and an organic solvent which is virtually immiscible with water, such as, for example, ethyl acetate, and a weakly alkaline pH is established. The organic phase is separated off, and the aqueous phase can optionally be reextracted. The organic phase is dried, for example with magnesium sulphate, and filtered, and the filtrate is concentrated, and a residue which essentially contains the product of the formula (I) is obtained.

3-Trichloromethyl-pyridine to be prepared by the process according to the invention can be used as an intermediate for the preparation of herbicides (cf. EP-A 65,358) or of insecticides.

A typical reaction sequence for the preparation of an insecticidal active compound may be shown by way of example:

tion P 3,842,358, which is earlier with regard to the present application, but has not previously been published.

Reaction step e) is carried out in accordance with European Patent Application EP 0,192,060 A1, which has been published.

Another preparation method of an insecticidal active compound is shown below:

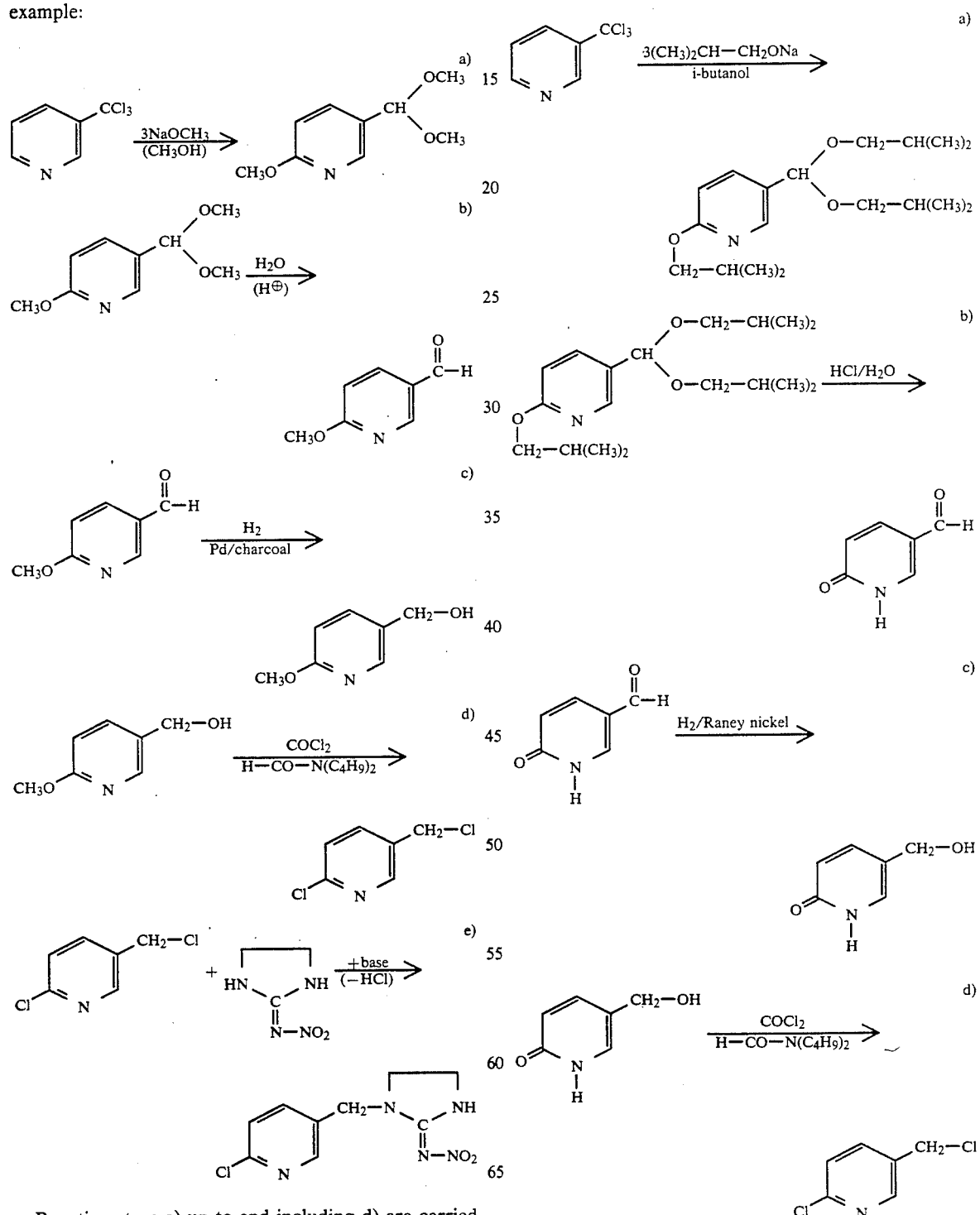

Reaction steps a) up to and including d) are carried out here in accordance with German Patent Application

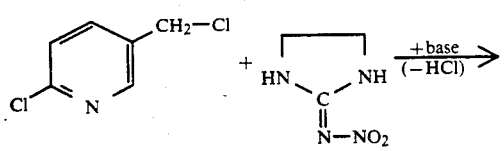

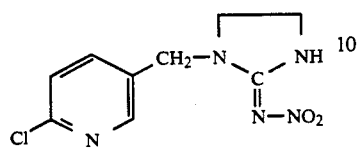

Reaction steps a) up to and including d) are carried out here in accordance with German Patent Application P 3,842,358, which is earlier with regard to the present application, but has not previously been published.

Reaction step e) is carried out in accordance with European Patent Application EP 0,192,060 A1, which has been published.

PREPARATION EXAMPLE

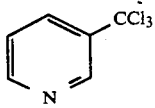

6.86 g (0.067 mol) of concentrated (96% strength) sulphuric acid is added dropwise to 6.0 g (0.0645 mol) of 3-methyl-pyridine in such a way that a temperature of 80° C. is reached and maintained by the exothermal reaction.

0.16 g (0.0013 mol) of benzamide is subsequently added, and the mixture is heated at 115° C. to 120° C. with the aid of an Osram 300 watt light bulb, which simultaneously acts as a light and heat source. At this temperature, a weak stream of chlorine is passed through the reaction mixture, which is present in the form of a melt, over a period of 14 hours. The light source is then removed, the reaction mixture is diluted at 70° C. with ethyl acetate and subsequently with ice-water, and a weakly alkaline pH is established with sodium carbonate. The organic phase is separated off, and the aqueous phase is re-extracted twice with ethyl acetate. The combined organic phases are dried with magnesium sulphate and filtered. The solvent is carefully removed from the filtrate by distillation under a water pump vacuum.

This gives 10.7 g (83% of theory) of 3-trichloromethyl-pyridine as a pale yellow, liquid residue of purity 98% (determined by gas chromatography).

The product can be purified further by vacuum distillation (boiling point: 105° C.–107° C./15 mbar).

It is understood that the specification and examples are illustrative but not limitative of the present invention and that other embodiments within the spirit and scope of the invention will suggest themselves to those skilled in the art.

We claim:

1. A process for the preparation of 3-trichloromethyl-pyridine of the formula

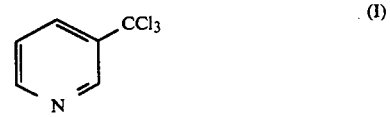

which comprises reacting 3-methyl-pyridine hydrogen sulphate of the formula

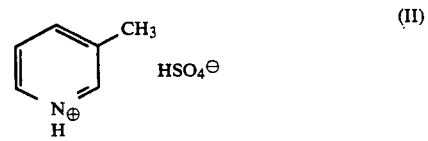

with elemental chlorine with exposure to at least one of visible and ultraviolet light at a temperature between about 70° C. and 150° C. in the presence of an aromatic carboxamide as catalyst.

2. The process according to claim 1, wherein the 3-methyl-pyridine hydrogen sulphate is produced and then reacted with the elemental chlorine in situ without intermediate isolation.

3. The process according to claim 1, wherein the catalyst is benzamide.

4. The process according to claim 1, wherein the light source emits at the border between visible and ultraviolet light.

5. The process according to claim 1, wherein the reaction is carried out at a temperature between about 90° C. and 130° C.

6. The process according to claim 1, wherein about 3 to 15 moles of elemental chlorine are employed per mole of 3-methyl-pyridine hydrogen sulphate.

7. The process according to claim 2, wherein the 3-methyl-pyridine hydrogen sulphate is initially prepared by introducing 3-methyl-pyridine into a reaction vessel and adding an approximately equimolar amount of sulphuric acid at a temperature between about 20° C. and 100° C.

8. The process according to claim 7, including the further steps of establishing a reaction temperature between 90° C. and 130° C., adding the catalyst, slowly passing elemental chlorine into the reagent with exposure to light, and extracting the resulting reaction product with an organic solvent which is virtually immiscible with water.

* * * * *